United States Patent [19]

Holzwarth

[11] 4,440,225

[45] Apr. 3, 1984

[54] OIL RECOVERY USING MODIFIED HETEROPOLYSACCHARIDES IN BUFFERED BRINE

[75] Inventor: George M. Holzwarth, Linden, N.J.

[73] Assignee: Exxon Research and Engineering Co., Florham Park, N.J.

[21] Appl. No.: 417,439

[22] Filed: Sep. 13, 1982

[51] Int. Cl.³ .............................................. E21B 43/22
[52] U.S. Cl. .................................... 166/246; 166/275; 435/104
[58] Field of Search ................ 166/246, 275; 435/104; 536/114; 252/18.55 D

[56] References Cited

U.S. PATENT DOCUMENTS

| | | | |
|---|---|---|---|
| 3,020,207 | 2/1962 | Patton .................................... | 195/31 |
| 3,208,518 | 9/1965 | Patton .................................... | 166/246 |
| 3,355,447 | 11/1967 | O'Connell ............................ | 260/209 |
| 3,591,578 | 7/1971 | Colin et al. ........................... | 260/209 |
| 3,773,752 | 11/1973 | Buchanan et al. ................... | 260/209 R |
| 3,801,502 | 4/1974 | Hitzman ............................... | 252/8.55 D |
| 4,096,073 | 6/1978 | Hitzman ............................... | 252/8.55 D |
| 4,119,546 | 10/1978 | Wernau ................................ | 252/8.55 D |
| 4,182,860 | 1/1980 | Naslund et al. ...................... | 536/114 |
| 4,296,203 | 10/1981 | Wernau ................................ | 435/104 |
| 4,394,447 | 7/1983 | Cadmus et al. ...................... | 435/104 |

OTHER PUBLICATIONS

Sandford et al., Extracellular Microbial Polysaccharides, Symposium, 172nd ACS meeting, ACS Symposium Series #45, pp. 192–210, (8/30–31, 1976).
Jeanes et al., J. Appl. Polymer Sic., vol. 5, pp. 519–526, (1961).
Patton, SPE paper No. 4670, 48th meeting of SPE of AIME, Las Vegas, 1973.
Holzwarth et al., Carbohydrate Research, vol. 76, pp. 277–280, (1979).

Primary Examiner—Stephen J. Novosad
Attorney, Agent, or Firm—James H. Takemoto; Jay Simon

[57] ABSTRACT

A process for recovering oil from a subterranean formation using a modified aqueous saline heteropolysaccharide solution as mobility control agent, said aqueous solution containing at least 0.5 wt. % of inorganic salts wherein the solutions are stabilized against loss of pyruvate groups on heat treatment by a process which comprises preparing an aqueous solution containing heteropolysaccharide and inorganic salts, adding a buffer to control pH between about 6.5 and 10.0, heating to a temperature of at least 100° C. and maintaining the pH at from 6.0 to 9.5 during heating, then removing cell debris. The buffered solutions do not suffer loss of pyruvate content which leads to viscosity loss.

9 Claims, No Drawings

OIL RECOVERY USING MODIFIED HETEROPOLYSACCHARIDES IN BUFFERED BRINE

BACKGROUND OF THE INVENTION

This invention relates to oil recovery using a modified heteropolysaccharide stabilized against pyruvate loss on thermal treatment. More particularly, the heteropolysaccharide used for oil recovery is prepared using a thermal treatment carried out in the presence of a buffered saline heteropolysaccharide solution.

U.S. Pat. No. 4,182,860 describes a process for preparing a modified heteropolysaccharide derived from bacteria of the genus Xanthomonas using a saline heat treatment which results in improved filterability of the so-treated heteropolysaccharide. The saline heat treatment, however, results in a ~20% loss of pyruvate groups. Sanford et al., Extracellular Microbial Polysaccharides, Symposium presented at 172nd Meeting of the American Chemical Society, ACS Symposium Series No. 45, Sandford and Laskin ed., pages 192–210 describe Xanthan heteropolysaccharides of differing pyruvic acid content. This paper shows that pyruvate content affects polysaccharide properties such as viscosity. Viscosity is in turn influenced by such factors as temperature, salt and pH. U.S. Pat. No. 3,801,502 discloses a method for producing waterflood bacterial viscosifiers wherein an alcohol, phenol, ketone or nonionic surfactant is added to fermentation effluent and the resulting mixture heated at temperatures between 50° C. and its boiling point until the desired viscosity is attained. Water or brine may be used as a reaction medium. U.S. Pat. No. 3,773,752 teaches a process for recovering polysaccharides from a heteropolysaccharide solution which comprises diluting the heteropolysaccharide solution with a salt solution until a desired viscosity is attained. Coagulation can be achieved by heating to a temperature below the boiling point of the mixture.

It is well known to add buffers to fermentation broth to optimize conditions for the fermentation process. In the case of bacteria of the Xanthomonas genus, a pH between about 6.0 to 7.5 is preferred. $NA_2HPO_4$, $K_2HPO_4$, $NaH_2PO_4$ and $KH_2PO_4$ are buffers typically added for this purpose. For reference see U.S. Pat. Nos. 4,119,546 and 3,020,207.

Jeanes et al., J. Appl. Polymer Sci., 5, 519–526 (1961) describe the heat treatment of polysaccharide B-1459 wherein the polyscaccharide was dissolved in water containing 1% KCl at pH 6.5, heated at 90° C. for 30 min., cooled and precipitated. U.S. Pat. No. 3,591,578 teaches that polysaccharide degradation in the fermentation broth can be avoided by heating the broth prior to precipitation at a temperature of from 80° C. to 130° C. for 10–120 minutes at a pH of from 6.3 to 6.9. U.S. Pat. No. 3,355,447 relates to a method of preparing a Xanthomonas colloid of improved stability in which the fermentation beer is adjusted to pH 7.0 to 9.0, heated at temperatures of from 150° to 170° F. for at least 20 minutes.

Patton, SPE Paper No. 4670, 48th Annual Meeting of the SPE of AIME, Las Legas, 1973, reports on a xanthan gum which is modified by adding a base such as NaOH or KOH to the polymer to raise the pH to about 12, then heating to about 185° F. for a period of 5–20 minutes. U.S. Pat. No. 4,096,073 discloses a method for increasing the viscosity of fermenter suspensions containing Gram-negative microbial cells comprising contacting the suspension with a base to raise the pH to a value between 9 and 12, and then aging at 50°–212° F. for at least 5 minutes. Holzwarth et al., Carbohydrate Research, 76, 277–280 (1979) demonstrate that pyruvate of acetyl groups can be selectively removed from xanthan. Pyruvate groups were removed by heating a dilute saline solution of xanthan at pH 3 for 2 hours at 95° C.

It would be desirable to have a heteropolysaccharide which has been modified by saline heat treatment and which has a pyruvate content substantially unchanged from that of the starting heteropolysaccharide. An unchanged pyruvate content is desirable to obtain a viscosifier with optimal viscosifying properties.

SUMMARY OF THE INVENTION

It has been discovered that the pyruvate content of modified heteropolysaccharides can be stabilized against loss upon saline heat treatment if the pH is controlled during the heating step, and that the stabilized pyruvate content results in an improved mobility control agent for oil recovery. Accordingly, the process of the invention for recovering crude oil from a subterranean formation comprises injecting an amount effective to provide mobility control of an aqueous solution containing a heteropolysaccharide produced by the action of bacteria of the genus Xanthomonas, driving the displaced oil through the formation and recovering the displaced oil, wherein said heteropolysaccharide has been prepared by a process comprising the steps of:

(a) preparing an aqueous solution which contains (i) from about 200 to about 30,000 parts per million by weight, of a heteropolysaccharide product produced by the bacterial fermentation of bacteria of the genus Xanthomonas, and (ii) at least about 0.5 weight percent of at lease one inorganic salt to obtain a saline heteropolysaccharide solution;

(b) adding a buffer, said buffer being characterized by having a pH and a buffer capacity such that the saline heteropolysaccharide solution has a pH of about 6.5 to 10.0 and a pH of about 6.0 to 9.5 during heating;

(c) heating said saline heteropolysaccharide solution to a temperature of at least about 100° C.;

(d) maintaining said saline heteropolysaccharide solution at a temperature of at least about 100° C. for a period of time sufficient to increase the injectivity and filterability characteristics of the heteropolysaccharide;

(e) maintaining said saline heteropolysaccharide solution at a pH of from about 6.0 to 9.5 during the heat treatment; and (f) removing or separating the proteinaceous materials and/or residual whole bacterial cells or other cell debris from the saline and heat-treated heteropolysaccharide product to thereby obtain a modified heteropolysaccharide capable of imparting a viscosity of at least 4.0 centipoises to an aqueous test solution containing 2 weight percent NaCl and 0.2 weight percent $CaCl_2$ when said modified hetterpolysaccharide is added to said solution at a concentration of approximately 600 parts per million, by weight, as measured on a Brookfield viscosimeter with a UL adapter at 60 rpm at 25° C. and said modified heteropolysaccharide is further capable of imparting a filterability such that more than 1000 ml of a different aqueous test solution containing 8.8 weight percent salt comprised of NaCL and $CaCl_2$ on a 10:1 weight ratio and approximately 600 parts per million concentration, by weight, of said modified heteropolysaccharide will pass without plugging through a Millipore ® filter having a diameter of 13 mm and a pore size of about 5 microns at a constant pressure drop of about 1.55 psig.

DETAILED DESCRIPTION OF THE INVENTION

Heteropolysaccharides are generally fermentation products produced by the action of bacteria, fungi, or yeasts on carbohydrates. Typical carbohydrates are glucose, sucrose, fructose, maltose, lactose, soluble starches and the like. Preferred carbohydrates are commercially available unrefined products such as raw sugar, molasses and the like. Representative bacteria include *Xanthomonas campestris, Xanthomonas phaseoli, Xanthomonas malvacearum, Xanthomonas carotae, Xanthomonas translucens, Xanthomonas hederae, Xanthomonas papavricola, Xanthomonas begoniae,* and *Xanthomonas incanae. Xanthomonas campestris, Xanthomonas begoniae* and *Xanthomonas incanae* are perferred species.

Heteropolysaccharides are produced using fermentation techniques well known in the art. The polysaccharide products are generally prepared in sterilized medium which has been inoculated with the desired organism. The pH of the medium is controlled in the range of 6 to 7.5 by adding a buffer such as $K_2HPO_4$ or a base, e.g., KOH or NaOH. This pH range has been determined as optimal for yield of polysaccharide while minimizing by-product formation. In typical commercial products, the heteropolysaccharide is isolated from the fermentation medium and sold as a dried powder, which can then be used to prepare a heteropolysaccharide solution or suspension. The crude, unpurified fermentation broth, however, is also commercially available and may be subjected to a saline heat treatment.

The salinity of the thickened aqueous solution or the broth is adjusted to bring the salt concentration to a level of about 0.5 wt. % or higher. For reasons not completely understood, these salts help protect the heteropolysaccharide from thermal degradation during heat transfer. Salt concentrations as low as 0.5 wt. % have been found effective, although salt concentrations on the order of 2 wt. % are generally preferred. Higher salt concentrations, up to the solubility limit of salt in the fermentation broth, do not adversely effect the solution. However, salt concentrations in excess of the solubility limit can, of course, interfere with the separation of the heteropolysaccharide from other components of the fermentation solution. Generally, it will be preferred to maintain the salt concentration at a level below 10 wt. % to avoid precipitation of inorganic salts and to avoid phase separation of the fermentation solution.

Salt solutions employed in the saline heat treating can be prepared from any one of a number of readily available and inexpensive substances. Inorganic salts containing sodium, calcium, magnesium, potassium, and barium as a cation and chloride, sulfate, carbonate, bicarbonate, and phosphate as an anion are suitable in the practice of this invention. However, salts such as sodium chloride and calcium chloride are generally preferred since they are readily available, relatively inexpensive and are compatible with most subterranean formations which is desirable when the polymer is to be used for oil recovery purposes. The salt chosen for use in this invention should, of course, be soluble to the desired level at the treatment temperature and should be stable. The salt should not be highly corrosive, toxic, or detrimental to the polymer in the solution. In the final analysis, the salt should be capable of protecting the polymer from degradation during heating. Simple viscosity measurements will enable one skilled in the art to determine whether a given salt is adequately performing this function.

At least one buffer is then added to the saline heteropolysaccharide solution. Preferred buffers are stable at temperatures of at least about 100° C., and are capable of maintaining a pH of from about 6.0 to 9.5, more preferably 6.5 to 9.5, and especially 6.5 to 7.5 at the elevated temperatures. Preferred buffers include sodium phosphate, potassium phosphate, imidazole, 2,4,6-trimethylpyridine, triethanolamine·HCl, N-ethylmorpholine, sodium pyrophosphate and tris(hydroxymethyl)aminomethane. Especially preferred buffers are sodium phosphate, potassium phosphate, sodium pyrophosphate and tris(hydroxymethyl)aminomethane. Buffer pairs may be employed.

During the saline heat treatment step, thermal energy is applied to the heteropolysaccharide-containing solution. In practical applications, the temperature will preferably be in the range of 100° C. to 180° C. and the temperature will be maintained within this range for a time period of at least one minute, preferably 30 to 300 minutes. The pH is also maintained in the range of 6.0 to 9.5 during heating. If necessary, additional buffers are added to provide pH control. Both the buffering capacity and ability to control pH of typical buffers are temperature dependent, and substantial changes may occur upon heating depending on the particular buffer system employed. Also, as the pH drops, more acidogenic groups are created which further lowers the pH thus creating more acidogenic group etc. This cycle leads to increasing pyruvate loss.

In the process of U.S. Pat. No. 4,182,860, modified polysaccharides are produced which contain about 20% fewer pyruvate groups per gram than native, unmodified polysaccharide, col. 7, lines 53–57. These results are demonstrated in Example XVIII. The process of the present invention, however, produces a modified polysaccharide whose pyruvate content is substantially unchanged.

It may be desirable to mechanically shear the heteropolysaccharide solution either before or after it has been subjected to the saline heat treatment. This shear can be conveniently imposed on the solution by a mechanical agitator, passing the solution through an orifice plate or other conventional means. Such shearing is not essential to the practice of this invention, but it assists in assuring that the components of the solution are totally solubilized, and it aids in subsequent operations.

Upon completion of the saline heat treatment, the crude heteropolysaccharide can be separated from the bacterial cells by centrifugation or filtration, if desired. Precipitation with methanol, ethanol, isopropanol, acetone, or similar agents permits the isolation of a relatively pure heteropolysaccharide. A biocide may also be added. The biocide is not essential to the practice of the invention but does protect the polymer solution from microbial degradation and improves its shelf life. Such biocides include any of a great variety known to the art. If the biocide to be used is heat-stable and will withstand the conditions of the particular saline heat treatment to be used, it may be added to the heteropolysaccharide solution prior to the heat treatment step.

Alternatively, biocide addition may be made after any desired dilution of the heat treated heteropolysaccharide solution has been accomplished.

Heat treating in a saline solution with subsequent filtration can be incorporated in the process steps for producing commercial grade heteropolysaccharide or alternatively, commercial grade heteropolysaccharide can be produced and then subjected to the treating process of this invention. For example, commercially available heteropolysaccharide can be obtained from a number of sources such as the products sold under the trade name Kelzan XC by Kelco Company. The commercial grade heteropolysaccharide is dissolved in water in a concentration of 200 to 300,000 parts per million in distilled water with the addition of from 0.5 to 10 weight percent salts. This solution is heated to a temperature ranging from 100° C. to 180° C. for a period of time ranging from 1 to 300 minutes. The heteropolysaccharide solution can then be subjected to mechanical separation to remove all entrained residual material such as clumps of incompletely solubilized heteropolysaccharide, residual proteinaceous material, and residual whole bacterial cells or other cellular debris. Further details concerning the saline heat treatment may be found in U.S. Pat. No. 4,182,860 which is incorporated herein by reference.

The techniques of secondary and tertiary oil recovery using heteropolysaccharides as mobility control agents are well known. In secondary recovery operations, the heteropolysaccharides are added to the waterflood to provide mobility control, i.e., to increase the viscosity of waterflood to value greater than that of displaced oil in order to minimize "fingering" effects which arise when a less viscous fluid is used to displace a more viscous fluid. Surfactants are typically added to waterfloods to improve the efficiency of the waterflooding process.

Tertiary recovery processes conventionally employ microemulsions as displacing agents. Microemulsions refer to a stable, transparent or translucent micellar solution or dispersion of oil, water or brine and at least one surfactant. Heteropolysaccharides may be incorporated into either the displacement fluid or the driver fluid as a means of providing mobility control.

The pyruvate stabilized modified heteropolysaccharides of the invention are further illustrated by the following example.

Example 1

Heteropolysaccharide solutions (samples A and B) were prepared by dissolving Xanthan powder manufactured by Kelco Company and sold under the trade name Kelzan XC in water with stirring. NaCL and CaCl$_2$ were added to samples A and B to achieve a final concentration of 3000 ppm Xanthan heteropolysaccharide, 2 wt. % NaCl and 0.2 wt. % CaCl$_2$. In addition, sample B contained 0.06 wt. % of a tris(hydroxymethyl)aminomethane (Tris) buffer "pH 8.5".

Samples A and B were heated for 90 minutes at 121° C., then serially filtered through 1.2, 0.8, 0.65, and a final 0.45 micron Millipore ® filter. The filtered polymer solution was then diluted with brine to achieve a final solution containing 600 ppm Xanthan, 8% NaCl and 0.8% CaCl$_2$. The resulting solutions were tested for viscosity, injectivity and pyruvate content. Viscosity was measured on a Brookfield LVF viscosimeter at 30° C. and 60 rpm using an LV-2 spindle. Injectivity was determined by diluting 1 part by volume of polymer solution with 4 parts by volume of a filtered brine so as to achieve a final salt composition of 8% NaCl and 0.8% CaCl$_2$. The flow rate of the resultant 600 ppm heteropolysaccharide solution through a 5 micron Millipore ® filter was measured at pressure drop of 1.55 psi. Pyruvate content was measured by the lactate dehydrogenase—NADH method described by Duckworth and Yaphe in Chem. and Ind. (Gr. Britain) 1970, 747. The results are summarized in the following table.

TABLE 1
EFFECT OF BUFFER ON THE PROPERTIES OF HEAT-TREATED XANTHAN

| | Sample A | Sample B |
|---|---|---|
| Heat Treatment | | |
| Polymer concentration, ppm | 3000 | 3000 |
| Salts | 2% NaCl | 2% NaCl |
| | 0.2% CaCl$_2$ | 0.2% CaCl$_2$ |
| Buffer | None | 0.06% Tris "8.5" |
| Time, min. | 90 | 90 |
| Temperature, °C. | 121 | 121 |
| Filtration, serial, to final | 0.45 | 0.45 |
| Millipore Filter Pore Size | micron | micron |
| pH | | |
| Before heating | 4.8 | 8.2 |
| After heating | 4.3 | 7.4 |
| Viscosity | | |
| 3000 ppm concentrate in 2.2% brine, 60 rpm with LV-2 spindle | | |
| Before heating, cP | 175 | 150 |
| After heating, cP | 138 | 130 |
| 600 ppm dilution, in 8.8% brine, at 73 sec$^{-1}$ (60 rpm, UL), 25° C., cP | 5.7 | 6.3 |
| Injectivity; 600 ppm in 8.8% brine | | |
| ml/min @ 100 ml | 9 | 11 |
| ml/min @ 1000 ml | 4 | 4 |
| Total thruput, ml | >1000 | >1000 |
| Pyruvate Content, Percent of Unheated Control | 63 | 102 |

Example 2

This example demonstrates that heating xanthan solutions under acidic conditions without added buffer results in loss of pyruvate groups. 10 ml samples of 2000 ppm xanthan solution were heated at 95° C. in the presence of 1 ml oxalic acid solutions of varying concentration and then assayed for pyruvate content. The results are summarized in the following table:

TABLE 2

| Sample | Heating Time (Minutes) | Oxalic Acid - Molarity Added | pH | Fraction of Pyruvate Removed |
|---|---|---|---|---|
| C | 0 | 0.48M | ~2 | 0.007 |
| | 10 | | | 0.18 |
| | 20 | | | 0.28 |
| | 30 | | | 0.35 |
| D | 0 | 0.12M | ~2.2 | 0.006 |
| | 10 | | | 0.14 |
| | 20 | | | 0.26 |
| | 30 | | | 0.36 |
| E | 20 | 0.12M | 2.2 | 0.29 |
| | 20 | 0.03M | 2.5 | 0.26 |
| | 20 | 0.01M | 3.5 | 0.14 |
| | 20 | 0.12M* | 3.6 | 0.13 |

*pH adjusted to 3.6 by adding NaOH.

What is claimed is:

1. A process for recovering crude oil from a subterranean formation which comprises injecting an amount effective to provide mobility control of an aqueous solution containing heteropolysaccharides produced by the action of bacteria of the genus Xanthomonas, driving the displaced oil through the formation and recovering the displaced oil, wherein heteropolysaccharide has been prepared by a process comprising the steps of:

(a) preparing an aqueous solution which contains (i) from about 200 to about 30,000 parts per million by weight, of a heteropolysaccharide product produced by the bacterial fermentation of bacteria of the genux Xanthomonas, and (ii) at least about 0.5 weight percent of at least one inorganic salt to obtain a saline heteropolysaccharide solution;

(b) adding a buffer, said buffer being characterized by having a pH and a buffer capacity such that the saline heteropolysaccharide solution has an initial pH of about 6.5 to 10.0 and a pH of about 6.0 to 9.5 during heating;

(c) heating said saline heteropolysaccharide solution to a temperature of at least about 100° C;

(d) maintaining said saline heteropolysaccharide solution at a temperature of at least about 100° C. for a period of time sufficient to increase the injectivity and filterability characteristics of the heteropolysaccharide;

(e) maintaining said saline heteropolysaccharide solution at a pH of from 6.0 to 9.5 during the heat treatment; and (f) removing or separating the proteinaceous materials and/or residual whole bacterial cells or other cell debris from the saline and heat-treated heteropolysaccharide product to thereby obtain a modified heteropolysaccharide capable of imparting a viscosity of at least 4.0 centipoises to an aqueous test solution containing 2 weight percent NaCl and 0.2 weight percent $CaCl_2$ when said modified heteropolysaccharides is added to said solution at a concentration of approximately 600 parts per million, by weight, as measured on a Brookfield viscosimeter with a UL adapter at 60 rpm at 25° C. and said modified heteropolysaccharide is further capable of imparting a filterability such that more than 1000 ml of a different aqueous test solution containing 8.8 weight percent salt comprised of NaCl and $CaCl_2$ on a 10:1 weight ratio and approximately 600 parts per million concentration, by weight, of said modified heteropolysaccharide will pass without plugging through a Millipore ® filter having a diameter of 13 mm and a pore size of about 5 microns at a constant pressure drop of about 1.55 psig.

2. The process of claim 1 wherein the buffer is sodium phosphate, potassium phosphate, imidazole, 2,4,6-trimethylpyridine, triethanolamine·Hcl, N-ethylmorpholine, sodium pyrophosphate and tris(hydroxymethyl)-aminomethane.

3. The process of claim 1 wherein the heating is from 100° to 180° C.

4. The process of claim 1 wherein the heating in step (d) is maintained for from about 30 to 300 minutes.

5. The process of claim 1 wherein the inorganic salt concentration is from about 0.5 to 10 wt. %.

6. The process of claim 1 wherein the inorganic salt is sodium chloride, calcium chloride or mixtures thereof.

7. The process of claim 1 wherein the bacteria is *Xanthomonas campestris.*

8. The process of claim 1 wherein the pH is maintained in step (e) by adding additional buffer.

9. The process of claim 1 wherein the aqueous solution contains at least one surfactant.

* * * * *